(12) United States Patent
Lee et al.

(10) Patent No.: US 7,131,784 B2
(45) Date of Patent: Nov. 7, 2006

(54) UNIT DOSE DELIVERY SYSTEM

(75) Inventors: Robert Lee, Lake Elmo, MN (US);
Darin J. Meyertholen, Woodbury, MN (US); Bruce R. Broyles, Oakdale, MN (US); Daniel D. Krueger, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 219 days.

(21) Appl. No.: 10/798,649

(22) Filed: Mar. 11, 2004

(65) Prior Publication Data
US 2005/0201813 A1    Sep. 15, 2005

(51) Int. Cl.
*B43M 11/00* (2006.01)
*B43K 5/14* (2006.01)
*B43K 5/02* (2006.01)

(52) U.S. Cl. ............... 401/128; 401/132; 401/134; 401/41; 206/219

(58) Field of Classification Search ........ 401/132–135, 401/126–130, 40–43; 215/DIG. 8; 206/219, 206/220, 221, 222
See application file for complete search history.

(56) References Cited

U.S. PATENT DOCUMENTS

| 2,445,477 | A | 7/1948 | Folkman |
| 3,279,654 | A | 10/1966 | Pierick |
| 3,713,780 | A * | 1/1973 | Shapiro ............... 422/61 |
| 5,217,433 | A | 6/1993 | Bunin |
| 6,227,736 | B1 | 5/2001 | Sogaro |
| 6,419,414 | B1 * | 7/2002 | Broyles et al. ......... 401/132 |
| 6,447,476 | B1 | 9/2002 | Sogaro |
| 6,450,717 | B1 | 9/2002 | Salz |
| 6,543,612 | B1 | 4/2003 | Lee |
| 6,547,101 | B1 | 4/2003 | Sogaro |
| 6,613,021 | B1 | 9/2003 | Sogaro |
| 6,719,729 | B1 | 4/2004 | Sogaro |
| 2004/0089372 | A1 | 5/2004 | Higgins, Jr. et al. |

FOREIGN PATENT DOCUMENTS

| DE | 32 08 786 | 9/1983 |
| DE | 92 15 566 | 12/1993 |
| EP | 0 520 616 | 12/1992 |
| EP | 1 163 918 | 12/2001 |

* cited by examiner

*Primary Examiner*—David J. Walczak
(74) *Attorney, Agent, or Firm*—Peter L. Olson

(57) ABSTRACT

A container includes, in one embodiment, an outer housing holding a first mass of a first component of a composition, an inner housing holding a second mass of a second component of the composition, and a seal. The first component is a liquid and the mass of the second component conforms to a bottom and side wall of the inner housing. An interference fit exists between the outer housing and the inner housing such that the inner housing seals the first mass within the first chamber. The inner housing has an aperture in a side wall of the second chamber.

40 Claims, 6 Drawing Sheets

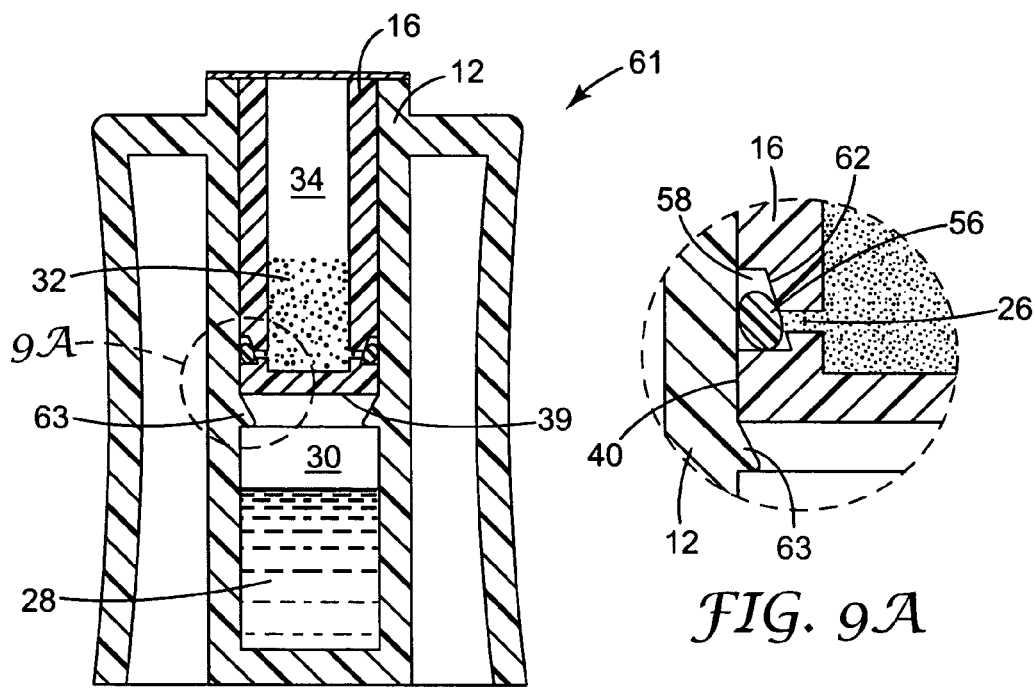
FIG. 9
FIG. 9A
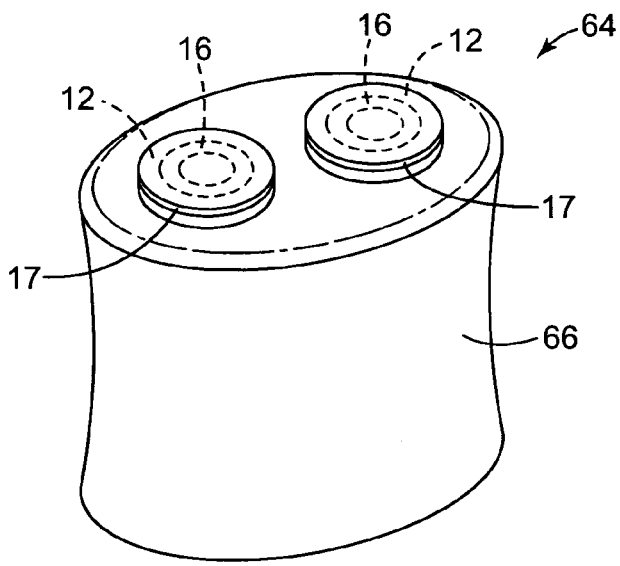
FIG. 10

UNIT DOSE DELIVERY SYSTEM

This invention relates to a delivery system for a composition made of two or more components, the assembly of a container for use in the system, a method for providing a composition, and a delivery system including an applicator and container.

BACKGROUND OF THE INVENTION

Many useful compositions are made of two components that are not normally mixed together until immediately prior to the time that a quantity of the composition is needed for use. For example, the components of epoxy-based adhesives are stored separately from each other, because once the components come into contact with each other a chemical reaction occurs that eventually turns the mixed composition into a hardened mass. For that reason, epoxy-based adhesives are widely available in packages that include two compartments or separate containers that keep the components of the adhesive initially isolated from each other.

Some packages for multiple-component compositions are relatively large and include a sufficient quantity of the components for multiple applications at different times. For example, epoxy adhesives are commonly available in bulk containers such as cans, jars and squeezable tubes. One component of the adhesive (often called "Part A") is supplied in one bulk container, and the other component (often called "Part B") is supplied in another container that typically matches the first container in shape and construction. Such bulk containers are in widespread use because the costs of packaging the components are relatively low.

To prepare an adhesive from the components stored in bulk containers, a quantity of each component is measured, withdrawn from the container and transferred to a mixing location. The mixing location may be a mixing well, a mixing pad or a third container. Next, the user mixes the components, using a spatula, brush or other suitable tool, and then transfers the mixed components to an application site.

However, the practice of supplying multiple-component compositions in two bulk containers is not entirely satisfactory. If, for example, the user does not withdraw the components from the bulk containers in the proper ratio, the characteristics of the resulting composition may be significantly affected. Additionally, the portion of each component that remains in its initial container may be adversely affected over a period of time by exposure to the atmosphere once that container is opened. The user is also compelled to dispose of the mixing pad, well or other mixing container after a single use, or undertake an effort to clean the same in preparation for a subsequent use. Furthermore, care must be taken to ensure that the component from one container is not inadvertently transferred to the bulk container of the other component, where it might contaminate that other component or initiate a chemical reaction that adversely affects the characteristics of that other component.

In recent years, there has been increased interest in "single use" containers for compositions made of two components that are initially kept apart from each other. Such containers typically avoid the need to measure out separate quantities of each component before mixing. These containers also help assure that the components, when mixed, are present in the desired ratio for the desired characteristics of the resulting composition. Additionally, if the components are mixed together within the container, the need for a mixing well, pad, container or other type of mixing structure is avoided.

Compositions made of two or more components that are initially kept separate from each other are widely used in the field of medicine and dentistry, including orthodontia. For instance, many adhesives and cements used in dentistry are made of two components that are not mixed together until immediately prior to use. Examples of two-component dental compositions include RelyX ARC dental cement and F2000 primer/adhesive, both available from 3M Company, St. Paul, Minn. Single use containers for multiple component compositions are especially convenient for storing medical and dental compositions, because the container along with the applicator can be disposed of after use for a single patient. In this manner, the risk of transferring an infectious disease from one patient to another is substantially reduced. Often, only a relatively small quantity of the composition is needed at any one time, and the smaller "single dose" or "single use" containers help ensure that a freshly-mixed batch of the composition is available when needed.

BRIEF SUMMARY OF THE INVENTION

The invention includes a delivery system for a composition made of two or more components, the assembly of a container for use in the system, a method for providing a composition, and a delivery system including an applicator and container. In one embodiment, the container includes an outer housing holding a first mass of a first component of the composition, an inner housing holding a second mass of a second component of the composition, and a seal. The first component is a liquid and the mass of the second component conforms to a bottom and side wall of the inner housing. An interference fit exists between the outer housing and the inner housing such that the inner housing seals the first mass within the first chamber. The inner housing has an aperture in a side wall of the second chamber.

BRIEF DESCRIPTION OF THE DRAWINGS

FIG. 9 illustrates a third embodiment of a container of the present invention.

FIG. 9A is an enlarged view of portion 9A in FIG. 9.

FIG. 10 is an exterior perspective view of a fourth embodiment of the present invention, illustrating a double dose unit container.

Figure 1:
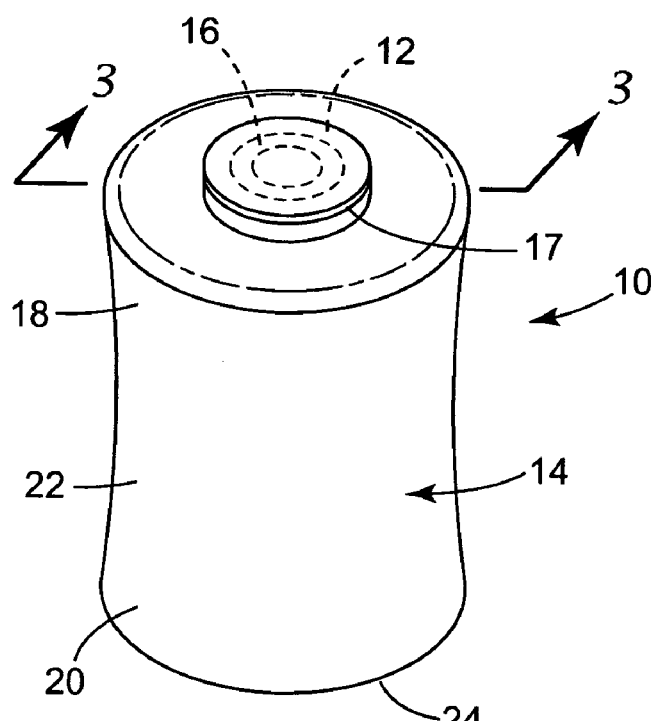
FIG. 1 is an exterior perspective view of a single dose unit container.

While the above-identified drawing figures set forth several embodiments of the invention, other embodiments are also contemplated. This disclosure presents the invention by way of representation and not limitation. It should be understood that numerous other modifications and embodiments can be devised by those skilled in the art which fall within the scope and spirit of the principles of this invention. The figures may not be drawn to scale. Like reference numerals have been used throughout the figures to denote like parts.

DETAILED DESCRIPTION

FIG. 1 is an exterior perspective view of a single unit dose container 10 of a delivery system for a composition. In the illustrated embodiment, container 10 includes outer housing 12, having outer skirt 14, and inner housing 16. A seal 17 is disposed over the outer housing 12 and inner housing 16. In one embodiment, container 10 contains a composition used in dental, pharmaceutical and medical procedures. Examples of suitable compositions include dental adhesives, etchants, sealants and primers. As used herein, the word "dental" includes all fields of dentistry including orthodontic and endodontic treatment.

Because container 10 typically holds a small volume of composition components, the storage chambers of container 10 can be vary small. Therefore, in one embodiment, outer skirt 14 is provided to enlarge container 10, thereby allowing for ease of handling. In the illustrated embodiment, outer skirt 14 is contoured to fit comfortably between the fingers of a user. In the illustrated embodiment, top section 18 and bottom section 20 each have a girth dimension which is greater than the girth dimension of middle section 22. In an exemplary embodiment, outer skirt 14 is substantially cylindrical, and thus each girth dimension is a circumference. In an exemplary embodiment, base 24 is flat and bottom section 20 is sufficiently wide to allow container 10 to rest stably upon a horizontal surface such as a countertop.

Figure 2:
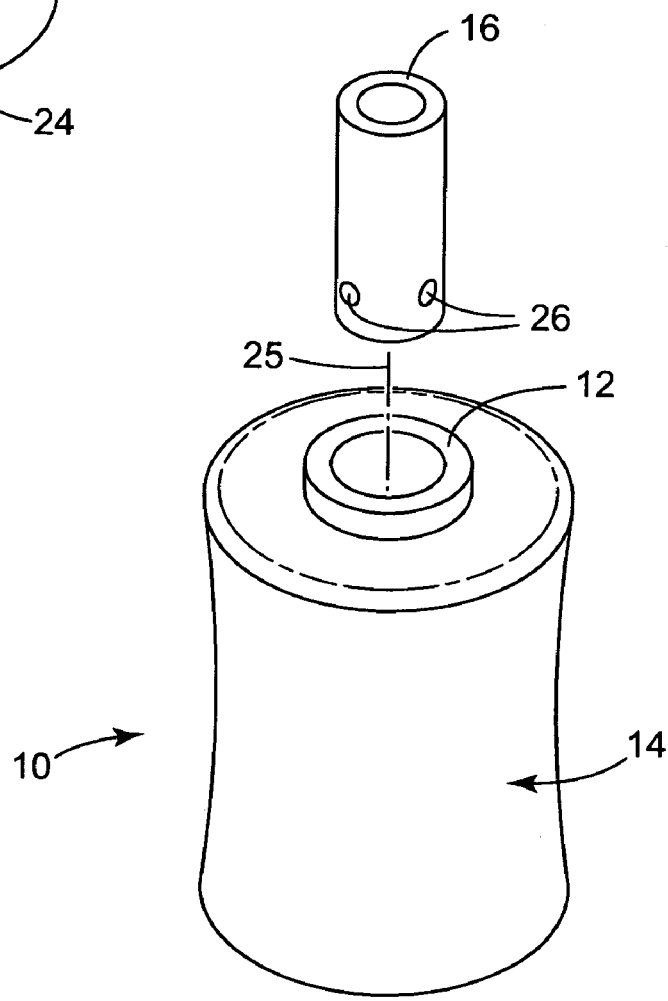
FIG. 2 is an exterior perspective view of the embodiment of FIG. 1, shown prior to assembly, with the inner housing removed from the outer housing.

FIG. 2 is an exterior perspective view of the embodiment of FIG. 1, shown prior to assembly, with inner housing 16 removed from outer housing 12 along axis 25. Inner housing 16 includes one or more apertures 26 in a side wall thereof to allow for the flow of a composition component from outer housing 12 into inner housing 16. While outer housing 12 and inner housing 16 are illustrated as cylindrical members, it is contemplated that any slidably mating shapes may be used.

Figure 3:
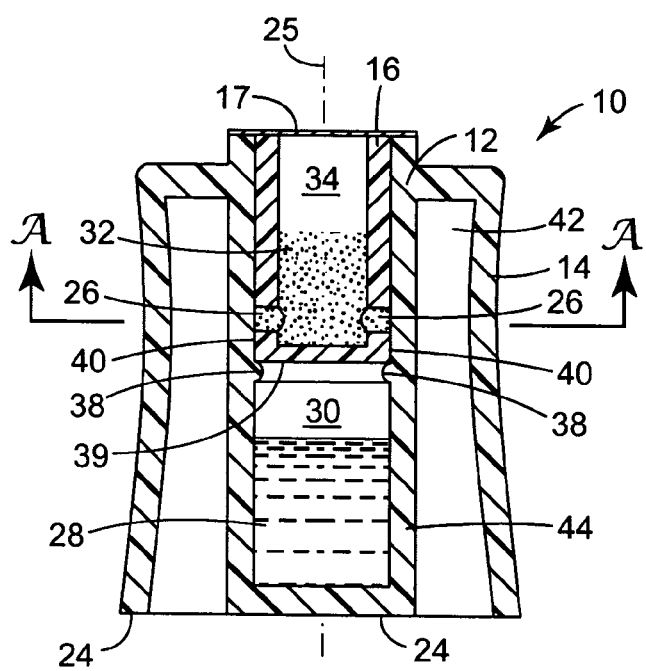
FIG. 3 is a sectional view of the embodiment of FIG. 1 taken along line 3—3.

FIG. 3 is a sectional view of the embodiment of FIG. 1 taken along line 3—3. Container 10 is designed to hold at least two masses of material separately from each other. This is especially useful for some dental compositions made of two or more components, for example, which should not be mixed until shortly before use. A first mass 28 of a first component of the composition is received within first chamber 30 of outer housing 12. A second mass 32 of a second component of the composition is received within second chamber 34 of inner housing 16. In an exemplary embodiment, hermetic seal 17 is provided across a top surface of outer housing 12 and inner housing 16. In an exemplary embodiment, stop member 38 is disposed within the first chamber 30 of outer housing 12 to establish a desired position of a bottom surface 39 of inner housing 16. In the illustrated embodiment, stop member 38 is a radially inward projection such as an annular rib on an inner surface of outer housing 12. Outer housing 12 and inner housing 16 are preferably sized to produce an interference fit between outer housing 12 and inner housing 16 at interface 40.

Container 10 is first assembled by providing outer housing 12 having outer skirt 14. In an exemplary embodiment, outer housing 12 includes a hollow space 42 between core 44 and outer skirt 14 for savings in materials, costs, and weight. In such an embodiment, base 24 need not be one contiguous piece, but may consist of a base section for core 44 and a ring-shaped base section for outer skirt 14 where container 10 is cylindrical. It is contemplated that outer skirt 14, and thereby container 10, can also be formed in other shapes.

First chamber 30 of outer housing 12 is at least partially filled with first mass 28 of a first component of the composition. Inner housing 16 is then inserted into outer housing 12. In one embodiment, inner housing 16 is in a proper position once a bottom surface 39 of inner housing 16 contacts stop member 38. While stop member 38 is not required, it is useful for preventing inner housing 16 from being inserted too far into outer housing 12. An interference fit at interface 40 between outer housing 12 and inner housing 16 is adequate in one embodiment to seal first chamber 30 and prevent migration of the first mass of material 28 into second chamber 34 (or out of the container 10 along interface 40 between an inner wall of outer housing 12 and an outer wall of inner housing 16). The interference fit is also adequate to prevent the migration of material contained within second chamber 34 into first chamber 30.

In the illustrated embodiment, inner housing 16 has one or more apertures 26 in a side wall thereof. Second chamber 34 is at least partially filled with a second mass 32 of a second component of the composition, conforming in shape to a bottom and side wall of second chamber 34. In an exemplary embodiment, first mass 28 consists of a liquid material and second mass 32 consists of a material in liquid, semi-liquid such as a gel or paste, or solid form, for example. Even in solid form, it is preferable that the material of second mass 32 is in a flowable form such as a powder. When the second mass of material 32 is introduced into second chamber 34, it fills apertures 26 as well as a bottom portion of second chamber 34.

Seal 17 is provided over at least inner housing 16 to prevent escape of material from second chamber 34. As shown, a top surface of outer housing 12 is flush with a top surface of inner housing 16 and seal 17 also extends across the top surface of outer housing 12. In an exemplary embodiment, seal 17 is bonded to a top surface of outer housing 12 and to a top surface of inner housing 16. In an exemplary embodiment, seal 17 hermetically seals first mass 28 and second mass 32 within container 10. In an exemplary, embodiment, seal 17 is a foil seal which can be broken in one or more manners, for example: by removing seal 17 by peeling it off container 10, or by rupturing seal 17 by the insertion of an object with manual force, preferably along axis 25, which is substantially perpendicular to an orientation of seal 17. In an exemplary embodiment, container 10, hermetically sealed as shown, provides a container 10 for the separate component masses 28 and 32 which has a sufficiently long shelf life and is suitable for distribution and storage without the need for additional packaging (i.e., no additional foil sealed pouch is necessary for storage of container 10 or the components therein).

Figure 3A:
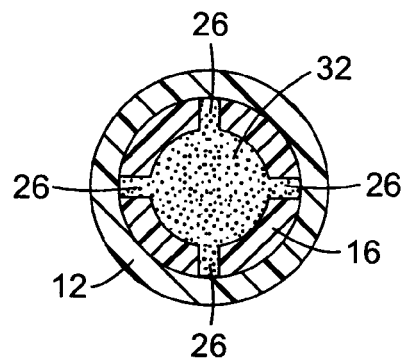
FIG. 3A is a sectional view of one embodiment of FIG. 3 taken along line A—A.
Figure 3B:
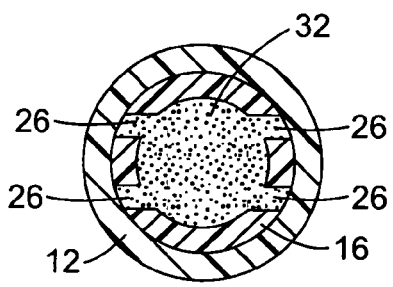
FIG. 3B is a sectional view of another embodiment of FIG. 3 taken along line A—A.

In the illustrated embodiment, inner housing 16 is cylindrical and each aperture 26 is a cylindrical bore. In one embodiment including a plurality of apertures 26, the apertures 26 are preferably equally spaced about a periphery of the side wall of inner housing 16 (see, e.g., FIG. 3A, where each aperture 26 is symmetrical about a radius of the cylinder of inner housing 16). In an alternative embodiment including a plurality of apertures 26, the apertures 26 are parallel to one another (see, e.g., FIG. 3B). Other numbers, shapes, orientations, and positions of aperture 26 can also be used.

Figure 4:
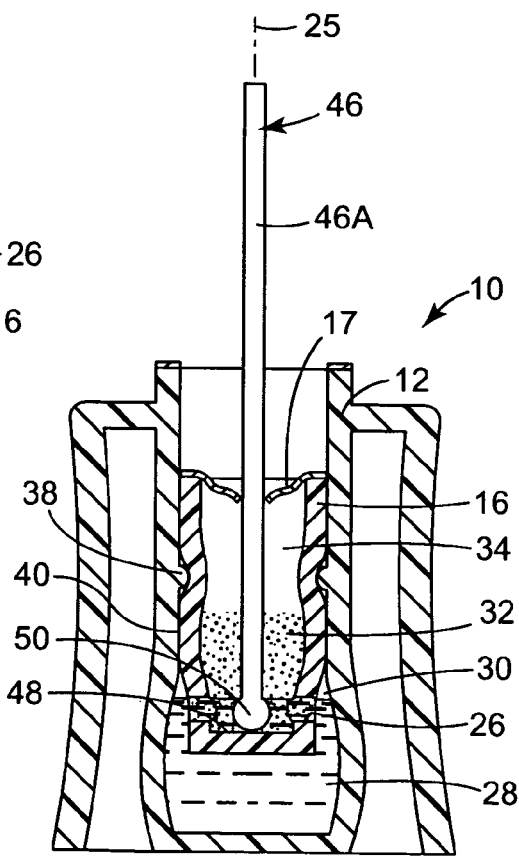
FIG. 4 is a sectional view of the embodiment of FIG. 3 in a subsequent step, with the inner housing pushed downward relative to the outer housing.

FIG. 4 is a sectional view of the embodiment of FIG. 3, showing how container 10 is used to mix and dispense the component 28 and 32 masses. Inner housing 16 is pushed downward relative to the outer housing 12. Outer housing 12 and inner housing 16 are each preferably formed by injection molding a deformable or flexible material such as polypropylene, polyethylene, or cyclic olefin copolymer, for example. There are compositions that may require the presence of oxygen during storage to improve chemical stability, such as methacrylate based dental adhesives, for example. In these situations, the aforementioned housing plastics are particularly suitable materials since they allow for oxygen transfer, thereby resulting in longer shelf life, reduced requirements for stabilizers in the composition components, and smaller air volume requirements in container 10.

Rod member 46, such as a composition applicator having a first end and a second end, is forced downward through seal 17, thereby breaking seal 17. Force from applicator 46 on second mass 32 and on inside surface 48 of inner housing 16 causes inner housing 16 to move downward relative to outer housing 12. Because of the seal between inner housing 16 and outer housing 12 at interface 40, this downward pressure causes the expansion of the walls of first chamber 30 or the deflection inward of the walls of second chamber 34, or both, resulting in the component mixing situation shown in FIG. 4. The extent of expansion/contraction is exaggerated in FIG. 4 for purposes of illustration. At this stage, the first mass of material 28 enters apertures 26 of inner housing 16 to mix with the second mass of material 32 therein. The pressurized situation causes turbulent jets of material from mass 28 to enter into second chamber 34, thereby producing an intensive mixing effect between the materials of both masses 28 and 32. In a case where second mass 32 consists of a solid material, it is preferable that the material is finely divided to facilitate this mixing. In most cases, no stirring is necessary to fully mix the first mass 28 of the first component of the composition with the second mass 32 of the second component of the composition. The mixing is completed simply by forcing inner housing 16 all the way down into chamber 30 of outer housing 12, resulting in mixed composition 49 within container 10 (see FIG. 5).

However, applicator 46 may be agitated within second chamber 34 to facilitate such mixing as desired. In an exemplary embodiment, applicator 46 includes elongated body 46A and tip 50 at a first end of the body 46A for application of mixed composition 49 to a desired surface. In one embodiment, tip 50 of applicator 46 has a generally spherical configuration, although other shapes are possible. Preferably, but not necessarily, tip 50 includes a material or structure that facilitates spreading of mixed composition 49 material across the surface to which mixed composition 49 material is to be applied. Tip 50 may include any suitable materials and structures that are compatible with mixed composition 49 and function to distribute mixed composition 49 over the receiving surface. Suitable materials and structures include foam and sponge materials or bristles or fibers that serve as a brush and that are applied to all or only part of tip 50.

Figure 5:
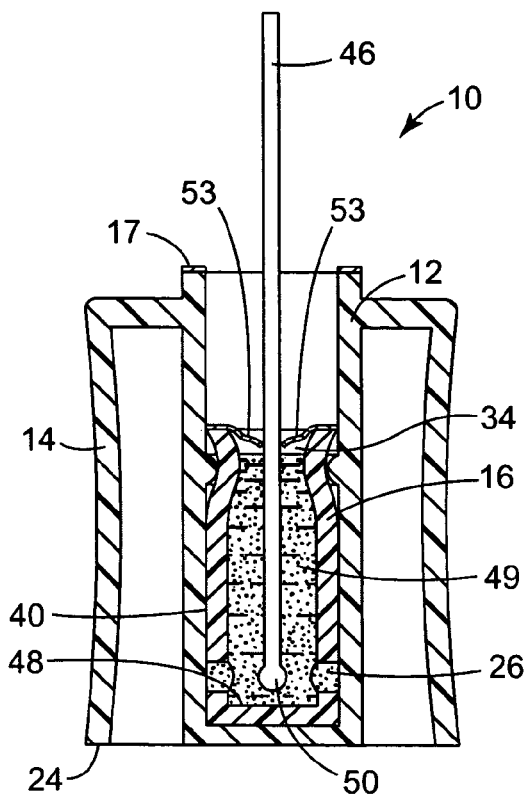
FIG. 5 is a sectional view of the embodiment of FIG. 4 in a subsequent step, with the inner housing pushed down entirely into the outer housing.

FIG. 5 is a sectional view of the embodiment of FIG. 4 in a subsequent step, with inner housing 16 pushed down entirely into outer housing 12. When applicator 46 has pushed inner housing 16 entirely down into outer housing 12, inner housing 16 acts as a positive displacement piston and displaces substantially all of the air and material mass 28 of first chamber 30. As a result, all of the material of first mass 28 enters through apertures 26 to mix with the material of second mass 32 and thereby form mixed composition 49. In an exemplary embodiment, mixed composition 49 is a homogenous compound made of two components, the first component provided by first mass 28 and the second component provided by second mass 32. In this manner, precise ratios of the first and second components of mixed composition 49 can be provided. In an exemplary embodiment, second chamber 34 is large enough to hold the combined volume of first mass 28 and second mass 32. In an exemplary embodiment, a chemical reaction occurs upon the mixing of the first component and the second component to form mixed composition 49, thereby resulting in a mixed composition 49 which is hardenable. Such a composition increases in hardness due to one or more influences, including for example, exposure to air, light, heat, or chemicals.

Dimensions for exemplary embodiments follow: Outer skirt 14 has a height greater than or equal to about 15 mm, less than or equal to about 30 mm, and preferably about 22 mm. Outer skirt 14 has a base 24 width greater than or equal to about 10 mm, less than or equal to about 30 mm, and preferably about 20 mm. Mixed composition 49 has a volume greater than or equal to about 50 microliters, less than or equal to about 300 microliters, and preferably about 120 microliters. Inner housing 16 has a diameter greater than or equal to about 3 mm, less than or equal to about 5 mm, and preferably about 4 mm. Inner housing 16 has a length greater than or equal to about 8 mm, less than or equal to about 20 mm, and preferably about 16 mm. Second chamber 34 of inner housing 16 has a volume greater than or equal to about 60 cubic mm, less than or equal to about 315 cubic mm, and preferably about 200 cubic mm. Outer housing 12 has an inner diameter greater than or equal to about 4 mm, less than or equal to about 7 mm, and preferably about 6 mm. First chamber 30 of outer housing 12 has a length greater than or equal to about 2 mm, less than or equal to about 5 mm, and preferably about 3.5 mm. First chamber 30 of outer housing 12 has a volume greater than or equal to about 30 cubic mm, less than or equal to about 150 cubic mm, and preferably about 100 cubic mm. Inner housing 16 includes about one or more apertures 26 and about ten or fewer apertures 26, and preferably about six apertures 26. Each aperture 26 is preferably a cylindrical bore having a diameter greater than or equal to about 0.5 mm, less than or equal to about 2.0 mm, and preferably about 1.0 mm. These dimensions and aperture numbers are provided as examples only; it is contemplated that container 10 can be made in any size suitable for a particular use or purpose.

Once mixed composition 49 has been formed from the first and second components, applicator 46 may be withdrawn so that mixed composition 49 material on tip 50 can be applied to a desired surface. It is preferable that tip 50 does not contact any other surface so as to prevent contamination. However, in some cases, fragments 53 of seal 17 may remain on a top surface of inner housing 16. Because the top surface of seal 17 has been exposed to the environment, it may be contaminated with bacteria, dirt or other undesirable contaminates. In the illustrated embodiment, great care must be taken to remove tip 50 without wiping mixed composition 49 on tip 50 with seal fragments 53 and without contaminating mixed composition 49 thereon.

Figure 6A:
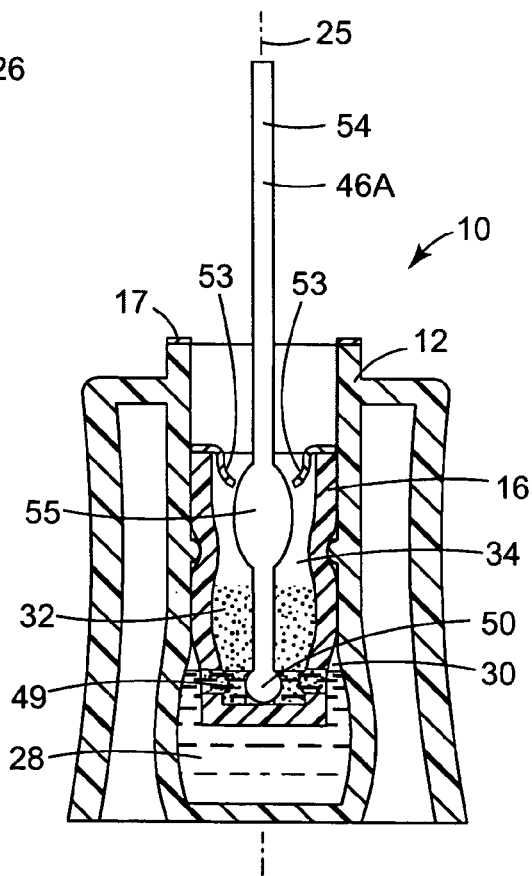
FIG. 6A is similar to FIG. 4 except that it shows an alternate embodiment of an applicator.

FIG. 6A is similar to FIG. 4 except that it shows an alternate embodiment of an applicator; applicator 54 includes projection 55 thereon along elongated body 46A of applicator 54. As projection 55 passes through broken seal 17, projection 55 pushes fragments 53 of seal 17 toward the inner surface walls of inner housing 16 and away from axis 25. In order to pass through broken seal 17, projection 55 is placed so that the widest part of projection 55 is no farther from a tip end of applicator 54 than the length of second chamber 34 of inner housing 16. Projection 55 has a girth dimension at a widest point which is greater than a girth dimension of body 46A. However, in an exemplary embodiment, projection 55 is small enough to pass into second chamber 34 of inner housing 16. In the case where body 46A is a cylinder and projection 55 is a solid ellipse, each girth dimension is a circumference. In one embodiment where inner housing 16 is cylindrical, the girth dimension of projection 55 at a widest point is less than an inner diameter of inner housing 16.

Compared to applicator 46 of FIG. 4, applicator 54 with projection 55 clears a larger area between fragments 53 of seal 17 for the extraction and reinsertion of tip 50 of applicator 54, thereby minimizing the chance of contamination of mixed composition 49 carried by tip 50. In an exemplary embodiment, projection 55 is a symmetrical solid ellipse which is tapered on both sides. However, it is contemplated that projection 55 can be of any shape having a girth dimension greater than a girth dimension of the elongated body 46A. Other shapes include, for example, disc, hemispherical, spherical, and cone shapes. While applicator 54 is useful with container 10 of the present invention, applicator 54 can also be used with any container having a rupturable seal at an opening of the container.

Figure 6B:
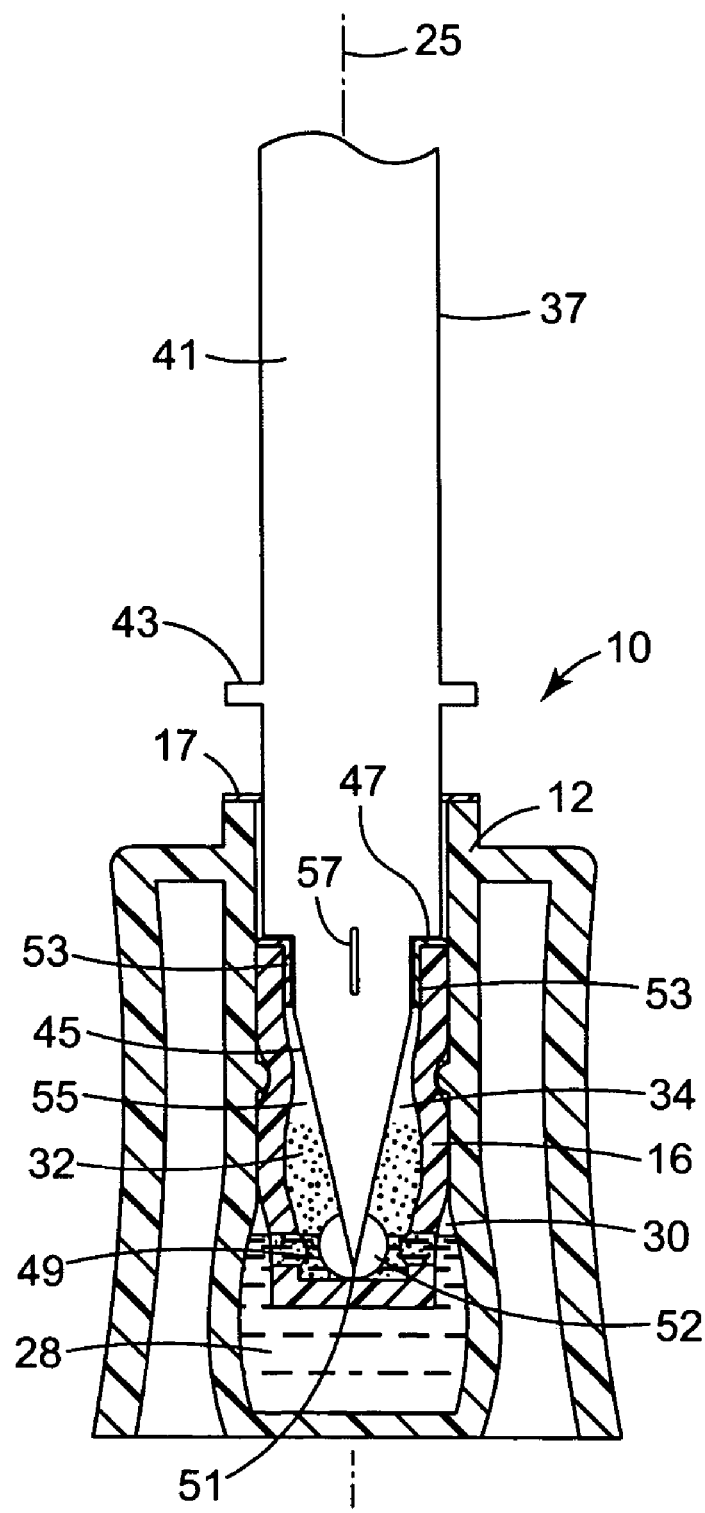
FIG. 6B is similar to FIG. 4 except that it shows yet another alternate embodiment of an applicator.

FIG. 6B is similar to FIG. 4 except that it shows yet another alternate embodiment of an applicator. In an exemplary embodiment, applicator 37 includes elongated body 41 having stop member 43 thereon. As illustrated, elongated body 41 interfaces with head 45 at shoulder 47. In an exemplary embodiment, head 45 tapers from a girth larger dimension proximate shoulder 47 to a smaller girth dimension at tip 51. In an exemplary embodiment, tip 51 has a sharp point to facilitate the breaking of seal 17. In an exemplary embodiment, tip 51 has brush elements 52 disposed thereon in a spherical configuration.

In an exemplary embodiment, applicator 37 is generally cylindrical and is sized so that shoulder 47, rather than tip 51, is used to push inner housing 16 into outer housing 12; in that case, the length of tapered head 45 is less than or equal to the length of second chamber 34 of inner housing 16. With applicator 37, the insertion of inner housing 16 into outer housing 12 is more easily accomplished because the interface between shoulder 47 and the top surface of inner housing 16 provides for a larger surface area for the application of the pushing force, compared with the surface area of tip 50 of applicator 46 of FIG. 4. In an exemplary embodiment, tapered head 45 has a larger dimension proximate shoulder 47 to push seal fragments 53 toward the inner walls of inner housing 16 and a smaller dimension proximate tip 51.

Tip 51 itself may be used for application of mixed composition 49 to a desired surface. In another embodiment, tip 51 may include application elements such as a plurality of brush elements 52. In an exemplary embodiment, stop member 43 is disposed about elongated body 41 and positioned so that a distance between shoulder 47 and stop member 43 is approximately equal to a distance between the top surfaces of inner housing 16 and outer housing 12 when inner housing 16 has been completely pushed into outer housing 12 (see FIG. 5). Thus, when stop member 43 contacts the top surface of outer housing 12, the contact signals to a user that complete mixing of component masses 28 and 32 has occurred to produce mixed composition 49. In one embodiment, body 41 is hollow and one or more air vent slots 57 are disposed on tapered head 45 to allow for pressure release during the insertion of inner housing 16 into outer housing 12. Other shapes for applicator 37 can be devised that fall within the scope of the invention. For example, head 45 may take on a different shape than illustrated. Moreover, elongated body 41 may be narrower but include wider flanges or projections to serve as shoulder 47 and stop member 43.

Figure 7:
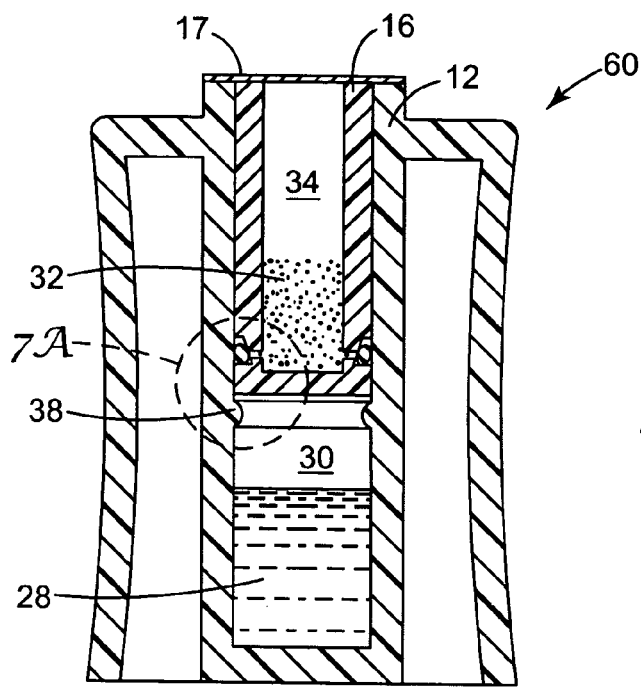
FIG. 7 illustrates a second embodiment of a container of the present invention.
Figure 7A:
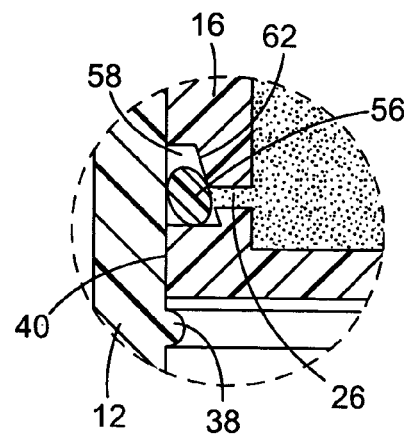
FIG. 7A is an enlarged view of portion 7A in FIG. 7.

FIG. 7 illustrates a second embodiment of a container 60 of the present invention. FIG. 7A is an enlarged view of portion 7A in FIG. 7. With some compositions, an interference fit between outer housing 12 and inner housing 16 at interface 40 may not be adequate to sufficiently seal first mass 28 from second mass 32. In such a case, or where there is not an interference fit at interface 40, a seal 56 may be utilized. In the illustrated embodiment, seal 56 is held within depression 58 proximate aperture 26. As with container 10, container 60 is assembled by at least partially filling first chamber 30 with a first mass 28 of a first component of a composition. Inner housing 16 is then inserted down into first chamber 30. Second chamber 34 is at least partially filled with a second mass 32 of a second component of the composition, conforming in shape to a bottom and side wall of second chamber 34.

Seal 56 is movably disposed within depression 58 so that seal 56 can move between sealed and unsealed positions. As inner housing 16 is first pushed downward into outer housing 12, seal 56 naturally migrates to a top portion of depression 58 and is pushed downward as inner housing 16 is pushed downward. However, seal 56, to be effective, should prevent material or gas flow between aperture 26 and outer housing 12. In an embodiment including stop member 38, inner housing 16 is inserted until stop member 38 is contacted. Then, inner housing 16 is pulled back up to seat seal 56 at a bottom portion of depression 58 in order to seal the area between outer housing 12 and aperture 26. A bottom section of outer housing 12 can also be squeezed in order to force inner housing 16 up relative to outer housing 12. Therefore, inner housing 16 does not rest upon stop member 38 in this case. To facilitate the seating of seal 56 at aperture 26, depression 58 includes a ramped wall 62, with the ramped wall 62 having a greater depth at a bottom portion of the wall than at a top portion of the wall. The directional terms "down" and "up" are used for purposes of explanation only, relative to the illustrated figures. The actual movement directions can of course be altered by changing the orientation of container 60.

In an exemplary embodiment, inner housing 16 is initially pushed down so that an upper surface of inner housing 16 is lower than an upper surface of outer housing 12. It is preferable that when inner housing 16 is pulled back up to seat seal 56, the upper surface of inner housing 16 is even with the upper surface of outer housing 12. Then, seal 17 can be provided over the upper surfaces of both inner housing 16 and outer housing 12.

Figure 8A:
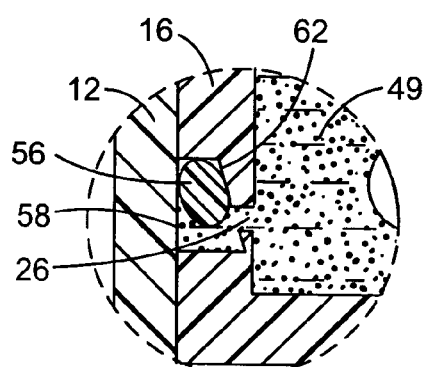
FIG. 8A is an enlarged view of portion 8A in FIG. 8.
Figure 8:
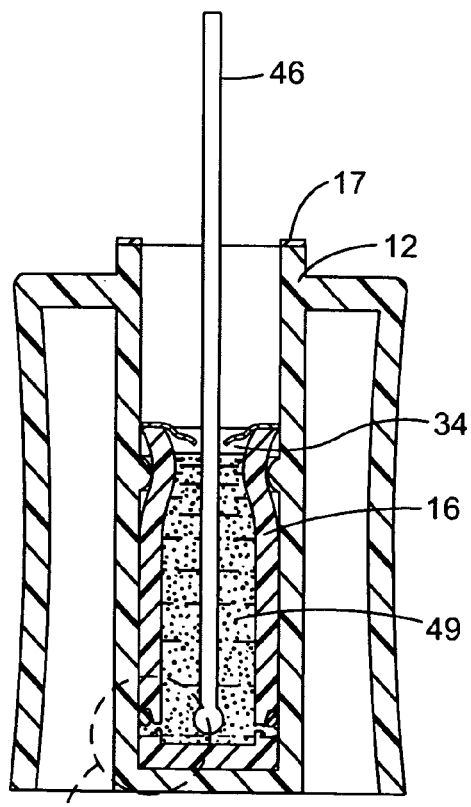
FIG. 8 shows the embodiment of FIG. 7 in a subsequent step, with the inner housing pressed down into the outer housing.

FIG. 8 shows the embodiment of FIG. 7 in a subsequent step, where mixing has occurred between component masses 28 and 32 to form mixed composition 49, with inner housing 16 pressed into outer housing 12. FIG. 8A is an enlarged view of portion 8A in FIG. 8. As inner housing 16 is pushed downward through first chamber 30 of outer housing 12, the downward force causes seal 56 to migrate to an upper portion of depression 58. This opens aperture 26 and allows for the movement of material of first mass 28 from first chamber 30 into second chamber 34 to mix with the material of second mass 32. In an exemplary embodiment, seal 56 is an o-ring and depression 58 is an annular groove in an outer surface of inner housing 16. FIG. 9 illustrates a third embodiment of a container of the present invention. FIG. 9A is an enlarged view of portion 9A in FIG. 9. Container 61 is similar to container 60 of FIG. 7 except that container 61 includes ramp member 63 to aid in the seating of seal 56 within depression 58. Ramp 63 may include a single ramp protrusion, multiple ramp protrusions, or a continuous ramp ridge disposed on an inner surface of chamber 30 of outer housing 12. Where multiple ramp protrusions are provided, it is preferable that they are disposed at equal intervals about an inner circumference of outer housing 12. Inner housing 16 is inserted so that a bottom surface of inner housing 16 moves onto the ramped surface of ramp 63, for example with the use of manual force. When the force is released, the shape of ramp 63 provides a spring effect, thereby pushing inner housing 16 back in a direction opposite from the direction of the applied force, and thereby seating seal 56 at a bottom portion of depression 58 in order to seal the area between outer housing 12 and aperture 26. The inclined surface of ramp 63 and/or seal 56 may be lubricated or otherwise treated to enhance the seating effect. It is important that inner housing 16 not be pushed in so far that ramp 63 falls into depression 58; in that case, inner housing 16 would not spring back relative to outer housing 12. Ramp 63 may be lengthened or provided with a stop member similar to stop member 38, for example, to prevent such an occurrence. Thus, while one shape is illustrated, it is contemplated that other reaction inducing shapes may be devised that fall within the scope of the invention.

FIG. 10 is an exterior perspective view of a fourth embodiment of the present invention, illustrating a double dose unit container. In container 64, a single outer skirt 66 surrounds two sets of outer housings 12 and corresponding inner housings 16, with their respective composition component masses separated by seals therein. Such a container 64 would be useful, for example, where two mixed compositions 49 are applied alternately or in quick succession. It is contemplated that numerous such variations and configurations are within the scope of the invention.

Although the present invention has been described with reference to preferred embodiments, workers skilled in the art will recognize that changes may be made in form and detail without departing from the spirit and scope of the invention.

The invention claimed is:

1. A delivery system for a composition, the system comprising a container, the container comprising:
   an outer housing having a first chamber and a top surface;
   a first mass of a first component of the composition, the first mass received in the first chamber;
   an inner housing received in the first chamber at a first position such that an interference fit exists between the outer housing and the inner housing such that the inner housing seals the first mass within the first chamber, the inner housing having a second chamber and a top surface, a bottom wall and a side wall, the inner housing having an aperture in the side wall of the second chamber;
   a second mass of a second component of the composition, the second mass received in the second chamber, and the second mass conforming to the bottom wall and the side wall; and
   a first seal which is bonded to the top surface of the inner housing and which is bonded to the top surface of the outer housing and which seals the second mass within the second chamber and which seals the first mass within the first chamber.

2. The delivery system of claim 1 wherein the container further comprises a stop member disposed on the outer housing wherein contact between the inner housing and the stop member occurs at the first position.

3. The delivery system of claim 2 wherein the stop member is an annular rib.

4. The delivery system of claim 1 wherein the seal is a foil seal.

5. The delivery system of claim 1 in which the outer housing further comprises an outer skirt surrounding the first chamber.

6. The delivery system of claim 5 wherein the skirt has a first girth dimension at a top section thereof, the skirt has a second girth dimension at a bottom section thereof, and the skirt has a third girth dimension at a section intermediate the top section and the bottom section, wherein the third girth dimension is less than the first girth dimension and the third girth dimension is less than the second girth dimension.

7. The delivery system of claim 1 wherein the container further comprises: a depression in an outer wall of the inner housing proximate the aperture; and a second seal positioned within the depression intermediate the aperture and the outer housing.

8. The delivery system of claim 7 wherein the depression has a first depth at a top section thereof and a second depth at a bottom section thereof, wherein the first depth is less than the second depth.

9. The delivery system of claim 7 wherein the second seal is an o-ring.

10. The delivery system of claim 7 wherein the outer housing further comprises a ramp.

11. The delivery system of claim 1 wherein a wall of the first chamber is flexible.

12. The delivery system of claim 1 wherein a wall of the second chamber is flexible.

13. The delivery system of claim 1 wherein the second component is a liquid.

14. The delivery system of claim 1 wherein the second component is a solid.

15. The delivery system of claim 1 wherein the inner housing is a cylinder and wherein the aperture is symmetrical about a radius of the cylinder.

16. The delivery system of claim 1 further comprising an applicator, the applicator comprising:
   an elongated body having a first end and a second end, the body having a first girth dimension;
   an applicator tip at the first end of the body; and
   a projection having a widest point positioned intermediate the first end and the second end, the projection having a second girth dimension at the widest point greater than the first girth dimension.

17. The delivery system of claim 16 wherein each girth dimension is a circumference.

18. The delivery system of claim 16 wherein the second chamber has a first length dimension and wherein a distance from the first end of the elongated body to the widest point of the projection is less than or equal to the first length dimension.

19. The delivery system of claim 16 wherein the inner housing has an inner diameter and wherein the second girth dimension is less than the inner diameter.

20. The delivery system of claim 16 wherein the applicator tip is a brush.

21. The delivery system of claim 1 further comprising an applicator, the applicator comprising:
    an elongated body having a first end and a second end;
    a head at the first end of the body, the head having a first end and a second end, the second end of the head being proximate the first end of the body, the head having a larger girth dimension proximate its second end and a smaller girth dimension proximate its first end; and
    a tip at the first end of the head.

22. The delivery system of claim 21 wherein the applicator further comprises:
    a shoulder disposed at an interface between the body and the head.

23. The delivery system of claim 22 wherein the applicator further comprises:
    a stop member disposed on the elongated body, a distance from the shoulder to the stop member being approximately equal to a distance between an upper surface of the inner housing and a upper surface of the outer housing when the inner housing is fully inserted into the first chamber of the outer housing.

24. The delivery system of claim 21 wherein the applicator further comprises:
    a plurality of brush elements disposed on the tip.

25. The delivery system of claim 21 wherein the body is hollow and the head comprises an air vent disposed thereon.

26. The delivery system of claim 1 wherein the inner housing includes a plurality of apertures in the side wall of the second chamber, the apertures being equally spaced about a periphery of the side wall.

27. The delivery system of claim 1 wherein the delivery system is used in a dental procedure.

28. The delivery system of claim 1 wherein the composition is hardenable.

29. A method of assembling a composition container comprising:
    providing an outer housing having a first chamber and a top surface;
    at least partially filling the first chamber with a first mass of a first component of the composition;
    inserting an inner housing into the first chamber until the inner housing is at a first position, wherein an interference fit exists between the outer housing and the inner housing such that the inner housing seals the first mass within the first chamber, the inner housing having a second chamber and a top surface, the second chamber having a bottom wall and a side wall, and the inner housing having an aperture in the side wall of the second chamber;
    at least partially filling the second chamber with a second mass of a second component of the composition; and
    sealing the second mass within the second chamber and the first mass within the first chamber by bonding a first seal to the top surface of the inner housing and to the top surface of the outer housing.

30. The method of claim 29 wherein the outer housing further comprises a stop member and wherein the step of inserting the inner housing into the first chamber includes sliding the inner housing into the first chamber until the inner housing contacts the stop member.

31. The method of claim 29 wherein the inner housing further comprises a depression in an outer wall of the inner housing proximate the aperture, the method further comprising:
    positioning a seal within the depression prior to inserting the inner housing into the first chamber in a first direction.

32. The method of claim 31 further comprising pulling back on the inner housing in a second direction opposite the first direction to seat the seal intermediate the aperture and the outer housing.

33. The method of claim 31 wherein the outer housing further comprises a ramp member, wherein the inner housing contacts the ramp member at the first position, and wherein the ramp member causes the inner housing to move in a second direction opposite the first direction to seat the seal intermediate the aperture and the outer housing.

34. A method of providing a composition comprising:
    providing a container, the container comprising:
    an outer housing having a first chamber and a top surface;
    a first mass of a first component of the composition, the first mass received in the first chamber;
    an inner housing received in the first chamber, the inner housing having a second chamber and a top surface, the second chamber having a bottom wall and a side wall, and the inner housing having an aperture in the side wall of the second chamber;
    a second mass of a second component of the composition, the second mass received in the second chamber; and
    a seal which is bonded to the top surface of the inner housing and which is bonded to the top surface of the outer housing and which seals the second mass within the second chamber and which seals the first mass within the first chamber;
    breaking the seal; and
    providing a force on the inner housing, thereby pushing the inner housing into the outer housing, wherein a pressure caused by the force forces the first mass through the aperture and into the second chamber to mix with the second mass to form the composition.

35. The method of claim 34 wherein the step of providing a force includes pushing downward on an applicator.

36. The method of claim 34 wherein the step of breaking the seal includes pushing downward on the seal with the applicator.

37. The method of claim 36 wherein the applicator comprises a projection and wherein the projection pushes broken parts of the seal toward an inner wall of the inner housing.

38. The method of claim 35 further comprising:
    agitating the composition with the applicator to further mix the first mass and the second mass.

39. The method of claim 34 wherein substantially all of the first mass enters the second chamber.

40. The method of claim 34 wherein the inner housing seals the first mass within the first chamber.

* * * * *